(12) United States Patent
Mahoney et al.

(10) Patent No.: US 9,351,739 B2
(45) Date of Patent: May 31, 2016

(54) TUNNELING DEVICE

(71) Applicants: John Mahoney, Marietta, GA (US);
Chris Staubly, Smyrna, GA (US);
Chase Dickerson, Atlanta, GA (US)

(72) Inventors: John Mahoney, Marietta, GA (US);
Chris Staubly, Smyrna, GA (US);
Chase Dickerson, Atlanta, GA (US)

(73) Assignee: Amendia, Inc., Marietta, GA (US)

( * ) Notice: Subject to any disclaimer, the term of this patent is extended or adjusted under 35 U.S.C. 154(b) by 402 days.

(21) Appl. No.: 14/145,532

(22) Filed: Dec. 31, 2013

(65) Prior Publication Data

US 2015/0182234 A1    Jul. 2, 2015

(51) Int. Cl.
*A61B 17/00*    (2006.01)
*A61B 17/16*    (2006.01)

(52) U.S. Cl.
CPC ......... *A61B 17/1642* (2013.01); *A61B 17/1671* (2013.01)

(58) Field of Classification Search
None
See application file for complete search history.

(56) References Cited

U.S. PATENT DOCUMENTS

| | | | |
|---|---|---|---|
| 5,285,795 A | 2/1994 | Ryan et al. | |
| 5,322,505 A | 6/1994 | Krause et al. | |
| 5,695,513 A | 12/1997 | Johnson et al. | |
| 6,719,761 B1 | 4/2004 | Reiley et al. | |
| 6,875,219 B2 | 4/2005 | Arromon et al. | |
| 7,318,823 B2 | 1/2008 | Sharps et al. | |
| 7,503,920 B2 | 3/2009 | Siegal | |
| 7,842,041 B2 | 11/2010 | Liu et al. | |
| 7,918,874 B2 | 4/2011 | Siegal | |
| 7,959,634 B2 | 6/2011 | Sennett | |
| 8,048,030 B2 | 11/2011 | McGuckin et al. | |
| 8,096,985 B2 | 1/2012 | Legaspi et al. | |
| 8,128,633 B2 | 3/2012 | Linderman et al. | |
| 8,157,806 B2 | 4/2012 | Frigg et al. | |
| 8,277,506 B2 | 10/2012 | Krueger et al. | |
| 8,414,571 B2 | 4/2013 | Pellegrino et al. | |
| 2006/0247600 A1 | 11/2006 | Yeung et al. | |
| 2008/0234827 A1 | 9/2008 | Schaller et al. | |
| 2009/0149878 A1 | 6/2009 | Truckai et al. | |
| 2010/0298832 A1* | 11/2010 | Lau ................... | A61B 17/1642 606/80 |
| 2011/0015574 A1 | 1/2011 | Persat | |
| 2011/0265789 A1 | 11/2011 | Gabriel | |
| 2013/0012951 A1 | 1/2013 | Linderman | |

* cited by examiner

*Primary Examiner* — Sameh Boles
(74) *Attorney, Agent, or Firm* — David L. King

(57) ABSTRACT

A tunneling device (10) for introduction into a body via a linearly extending guide (100) is formed as an elongated tunneling device (10) having an end portion (10E) bent to a predefined curvature. The elongated tunneling device (10) when confined in the linearly extending guide (100) is confined lengthwise in the guide (100). Upon movement of the tunneling device, advancing past the guide (100) into the body, the end portion (10E) of the tunneling device (10) returns to the predefined curvature without requiring any external physical resistance of load forces to initiate the bending.

13 Claims, 4 Drawing Sheets

TUNNELING DEVICE

TECHNICAL FIELD

The present invention relates to a device for use in treatment of acute vertebral compression fractures for introduction into a vertebral body through a single straight passage formed through cortical bone into the cancellous bone via a straight conduit or sleeve wherein the device when entering past the cancellous conduit or sleeve into the bone cavity transitions from straight to curved.

BACKGROUND OF THE INVENTION

Treatment of vertebral compression fractures commonly employs vertebroplasty and kyphoplasty techniques. Vertebroplasty employs a percutaneous injection of PMMA (polymethylmethacrylate) in a fractured vertebral body via a trocar and cannula.

Kyphoplasty is a modification of percutaneous vertebroplasty. Kyphoplasty involves a preliminary step consisting of the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at higher viscosities and lower pressures into the collapsed vertebra since a cavity exists, when compared to conventional vertebroplasty.

Often in employing Kyphoplasty two straight entries are made into the spine and the inflatable tamp balloons are inflated to form two cavities into which a bone hardening stabilizing cement can be injected. These two points of entry are required because the balloon when entering straight is offset to the left or the right of a midline of the vertebrae as shown in prior art FIG. 1 illustrating one of the inflated balloons.

As a result, to expand the vertebrae to its normal or close to normal original height, the balloon tamp is inflated to lift both sides of the compressed vertebrae. Ideally, the procedure should position the inflatable balloon tamp so it is centered crossing the midline. To accomplish this, the tunneling device must be manipulated in some way to create a path that crosses the midline.

One way is to provide a steerable device; these devices are made of stainless steel and have an internal tensile member that collapses a hinged portion of the outer shaft causing the tip to deflect. This results in a wide windshield wiper motion or sweeping path that does not form a precise tunnel that a balloon tamp can follow to a desirable known position. Steerable devices typically are made as multi-piece structures which are limited in strength running the risk of breakage and leaving portions of a broken device in the patient. These steerable devices all require a physical external manipulation or load to steer the tunnel device.

An alternative is a tunnel device having slots cut in a shaft or cannula to create an effective hinge that collapses under a load or resistance as the device advances in the soft cancellous bone tissue. These slots are cut such that the device bends along a curvature compressing the slots to close along the inside of the radius of curvature, preferably completely collapsing the slot that is to abut the side wall of the adjacent cut out wall. This abutting relationship strengthens the device as it tunnels through the tissue. In this prior art solution the desired curvature can only be achieved by the slots or cuts collapsing under the load created by the patient's tissue resisting the tunnel movement, accordingly, dependent of the patient's anatomy and the force required to close the slots, the device may have an indeterminate tunnel path. In fact, the device may only turn or bend when it upon contact with the hard cortical bone on the opposite side of the vertebrae. The functionality of these devices is dependent on the patient's bone density. These type devices may deflect prematurely, effectively creating a "wind-shield wiper" type cavity in comparatively dense bone, e.g. partially healed fracture, or the device may not deflect at all due to various pathologies that decrease bone density, e.g. osteoporosis.

Ideally, the tunnel device must be capable of achieving a consistent and predictable path that, in the case of vertebrae compression fracture repair, cross the midline to create a balloon tamp path that forms a cavity in the optimal location so the procedure can be accomplished with a single, preferably, small opening.

While the tunnel device of the present invention addresses these issues, it has further applications in any procedure where a single surgical entry requires curvature or bend in a path after entry into a body. This is made possible by the invention as disclosed herein as follows.

SUMMARY OF THE INVENTION

A tunneling device for introduction into a body via a linearly extending guide is formed as an elongated tunneling device having an end portion bent to a predefined curvature. The elongated tunneling device when confined in the linearly extending guide is confined lengthwise in the guide. Upon movement of the tunneling device, advancing past the guide into the body, the end portion of the tunneling device returns to the predefined curvature without requiring any external physical resistance of load forces to initiate the bending.

Preferably the tunneling device is an elongated rod. The rod can be a solid or non-hollow structure or optionally a hollow tube. The entry end portion can have a predefined curvature having one or more predetermined radii of curvature. In one embodiment, the curvature is defined by a single constant radius. Preferably, the device is curved such that a tangent to the maximum curvature at the end or tip of the entry end portion is offset from the straight projected path of the guide, inclined at a positive angle greater than 0 degrees, preferably at least 30 degrees, more preferably 45 degrees or more relative to the guide. This insures the tunneling device is sufficiently curved at the entry end portion when entering a vertebral body to cross a midline of the vertebrae for creating a path to properly center position a single balloon tamp as a functional example. Other examples requiring a curved tunnel device path include, but are not limited to positioning the device in a damaged soft tissue disk between adjacent vertebrae to facilitate delivery of biological tissue regeneration compositions including, but not limited to stem cells, collagen and additional dish tissue, beads or allograft particles or combinations thereof.

Preferably, at least the entry end portion of the tunneling device, if not the entire tunneling device is made from a shape memory material. The shape memory material of the device can be in a rod shape having a pre-set memory pre-set by heat to the predefined curvature. The shape memory material can be a metal or a polymer or a metal alloy. The metal alloy can be nickel titanium (NiTi) preferably nitinol (Nickel Titanium Naval Ordinance Laboratory). Alternatively, the shape memory material can be a ferromagnetic material that changes shape when exposed to a magnetic field to a predefined curvature to a pre-set defined curvature.

In the preferred embodiment, the tunnel device when formed from a rod includes a plurality of cut slots spaced on the rod along the entry portion. The slots are cut on an exterior side of the rod opposite the one or more radii of curvature. The inside surface of the rod is preferably uncut or smooth on the side adjacent the radius of curvature so the opposite outside surface having the cut slots align with the curvature. The cut slots open wider upon bending to the defined curvature. The cut slots are cut deep enough to provide sufficient flexibility in the curved entry end to allow it to easily straighten when confined in the guide, but by being on the opposite side of the radius of curvature insures the device is stiff in the tunneling direction to form the curved path in the soft tissue. This also insures the device can bend to its predefined curvature without any assistance or interference to the device returning to its predefined curvature by external steering forces or requiring any tissue resistance to achieve the bend. In fact, the device simply finds the correct pre-set predefined curvature simply by advancing past the confinements of the guide without any bending assistance. The guide preferably is a cannula device and due to the construction of the tunnel device, the cannula can be of an extremely small diameter, in one embodiment only 2 or 3 mm in diameter and the rod being smaller in size, about the size of a 10 to 13 gauge wire, slips easily in said guide cannula. This insures this is one of the smallest and most minimally invasive devices available for these types of procedures and it can further accomplish its task with only one single point of entry.

DEFINITIONS

"Bone fill, fill material, or infill material or composition" includes its ordinary meaning and is defined as any material for infilling a bone that includes an in-situ hardenable material or that can be infused with a hardenable material. The fill material also can include other "fillers" such as filaments, microspheres, powders, granular elements, flakes, chips, tubules and the like, autograft or allograft materials, as well as other chemicals, synthetics, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

The terms "Substantially" or "substantial" as used herein may be applied to modify any quantitative representation which could permissibly vary without resulting in a change in the basic function to which it is related.

"Osteoplasty" includes its ordinary meaning and means any procedure wherein fill material is delivered into the interior of a bone.

"Vertebroplasty" includes its ordinary meaning and means any procedure wherein fill material is delivered into the interior of a vertebra.

BRIEF DESCRIPTION OF THE DRAWINGS

The invention will be described by way of example and with reference to the accompanying drawings in which.

DETAILED DESCRIPTION OF THE INVENTION

Figure 1:
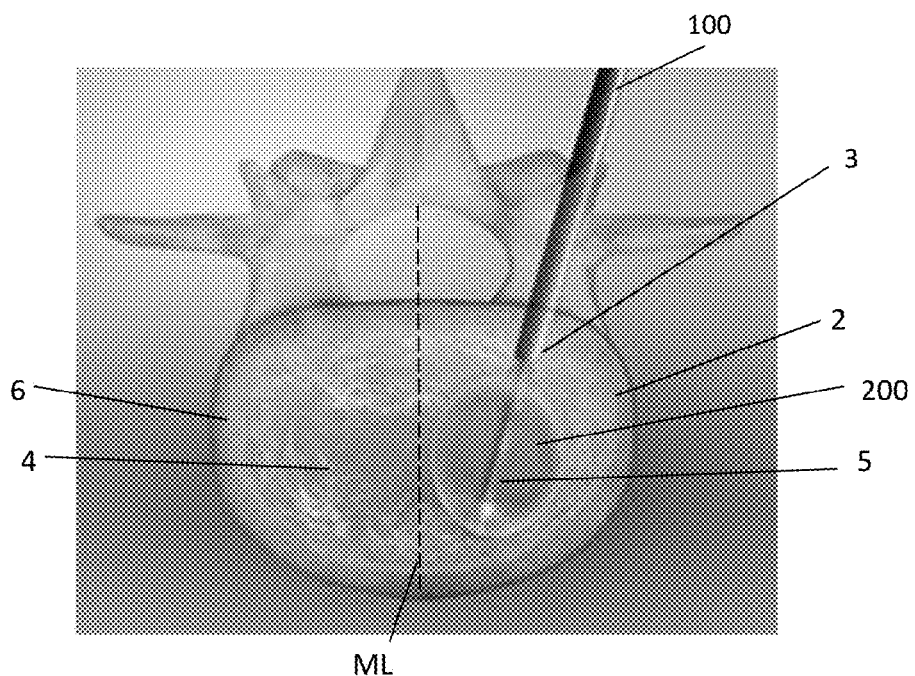
FIG. 1 is an image of a conventional straight insertion of a balloon tamp showing the offset relative to the midline of the vertebrae.

With reference to FIG. 1, a balloon tamp 200 is shown extending through a guide sleeve or cannula 100. The balloon tamp 200 is shown in an inflated condition. The balloon tamp 200 when expanded, compresses the soft tissue or cancellous bone 4 such that a void cavity 5 is created. When the straight line incision or opening 3 is created for the guide sleeve 100, it is known that the balloon tamp 200 when projecting inwardly on a straight line path is off center of the vertebrae. By being off the midline ML, the cavity 5 created is biased to the left or right side of the midline ML. As a result of this alignment relative to the midline ML, it is important that two openings are provided and a secondary procedure is applied on the opposite side (not illustrated). When that occurs, two cavities 5 are created to help stabilize the bone when bone cement or bone filler is added to the vertebral body 2 in a kyphoplasty procedure. By requiring two openings 3 to be created, the patient is subjected to twice the amount of trauma, and while these procedures are minimally invasive, the vertebral body 2 itself is in need of repair and therefore one should try to minimize the structural intrusion into the vertebral body 2 as much as possible. To accomplish this, various devices have been employed to try to provide a curved or angled path into the vertebral body 2 to form a cavity 5 in such a way to cross the rim of cortical bone so that it intersects the midline. When this is accomplished, only one incision will be required. To accomplish this, in the prior art, hinged devices have been provided that upon insertion meet the cancellous tissue and collapse along hinges closing the device in such a fashion that it can create a curved path crossing the midline. Alternatively, steerable devices have been provided wherein some mechanical mechanism and or external forces are used to manipulate the device which is inserted straight and then bent or maneuvered over; this creates a windshield wiping effect. Both of these are inferior procedures for creating a good path tunnel for the balloon tamp 200 to follow. It must be remembered that the tunneling devices are primarily designed to create a path or passageway that the balloon tamp 200 can easily follow upon being inserted into the vertebral body 2. If a swiping action or wide path is generated, it is uncertain where the balloon tamp 200 will end up as it is not effectively being guided by the passageway that was previously created. Accordingly, there is a need for an improved tunneling device in kyphoplasty procedures.

Figure 2:
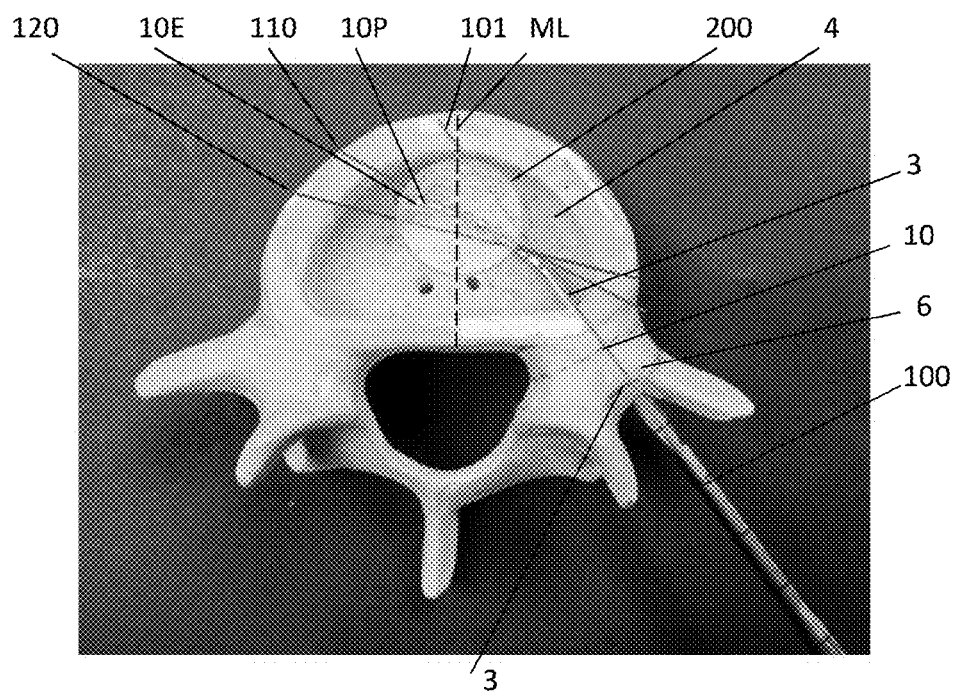
FIG. 2 is a photograph of a single entry into a vertebral model showing how the tunneling device curves to form a path crossing the midline.

With reference to FIG. 2, the improved tunneling device 10 of the present invention is illustrated. In this illustration, the guide sleeve 100 passes through the pedicle, through the cortical bone 6 creating an opening 3 through which the tunneling device 10 can then extend. As shown, the guide sleeve 100 is positioned off at an angle on the lower right hand side of FIG. 2 and the tunneling device 10 extends up into the cancellous bone 4 and as the tunneling device 10 leaves the guide sleeve 100, the device 10 at the end 10E initiates a predefined curvature having a curvilinear path 10P as illustrated. As shown, a straight line 110 projecting from the guide sleeve 100 which illustrates that the balloon tamp 200 as visualized by the circle would be centered on the midline, but if it followed the straight line 101 would have not intersected the midline ML or at least been offset. The center of the balloon tamp 200 would have been greatly offset relative to the midline ML of the vertebral body 2. However, by providing a curvilinear path 10P as found in the present invention, the balloon tamp 200 can be easily positioned right over the midline as shown by the line 110 extending tangent to the curved path and intersecting the center midline ML where the bone tamp 200 will be positioned. With reference to FIG. 2, there is a third line 120 shown where the curvature of the tunneling device 10 at the end portion 10E was increased; the balloon tamp 200 can be positioned even further inwardly towards the center of the cancellous bone 4 such that the balloon tamp 200 can be maneuvered along a path centered along the guide path 10P depending on the radius of curvature provided in the tunneling device 10 of the present invention.

Figure 3:
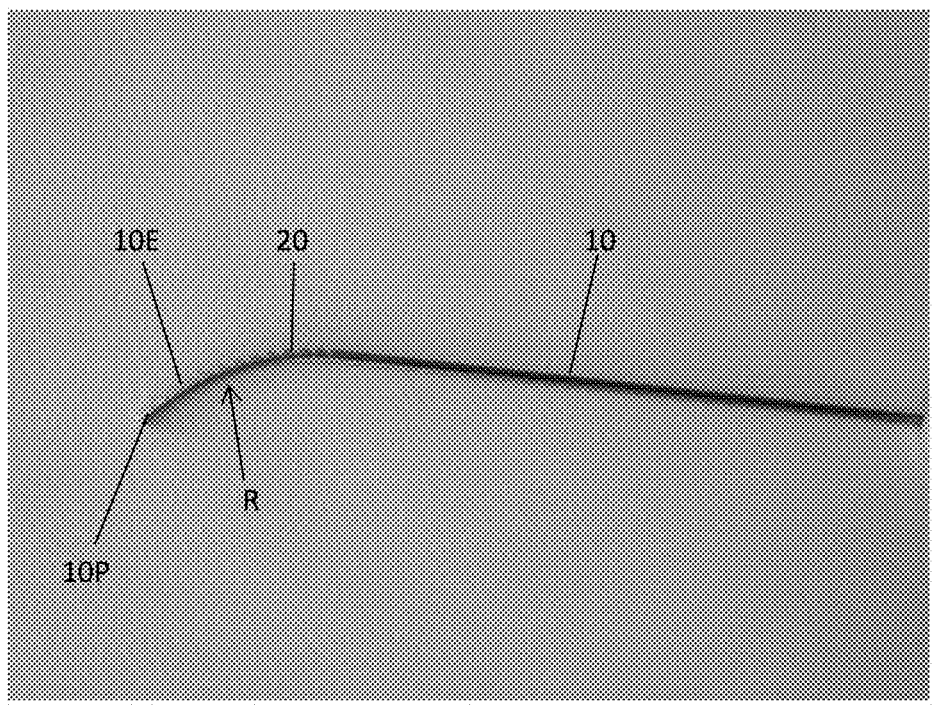
FIG. 3 is a perspective view of the end portion of the tunneling device of the present invention.

What is unique about the tunneling device 10 of the present invention is that it achieves its predefined curvature having a curvilinear path 10P without steering or any hingeable parts that collapse upon themselves due to any external resistance or forces. For example, the tunneling device 10 of the present invention is pre-set with a predefined curvature 10P. This curvature 10P is set in the material in such a fashion that the device 10 has a curved path in its normal state, in other words once the tunneling device 10 leaves the cannula or guide sleeve 100, the device 10 at the curved end 10E will automatically return to its unrestrained curved shape. This occurs the instant the device 10 starts to leave the cannula or guide sleeve 100, as such; the device 10 provides a curvilinear path 10P as illustrated in FIG. 3. An important feature of the device 10 is unlike hinged devices wherein collapsible slots are provided, the slots 20 are provided on an opposite side relative to the radius of curvature R. Hinged devices have the slots on the same side as the radius of curvature R, this allows the hinges to close upon resistance of the soft cancellous tissue as the device is driving into the vertebrae. The present invention has the slots 20 on the opposite side as shown, these slots 20 actually open and are provided to allow the end portion 10E of the tunneling device 10 to flex sufficiently that it can be straightened inside the guide sleeve 100. As illustrated, the guide sleeve 100 can be a cannula having a generally straight profile such that the tunneling device 10 contained therein will similarly initially be in a straight orientation prior to insertion. As the device 10 extends from the guide sleeve 100 into the vertebral body 2 and cancellous tissue 4 of the cavity, the device 10 will initiate its natural curvature 10P that has been predefined and pre-set. As shown in FIG. 3, a perspective view of the device 10 showing the radius of curvature R and the slots 20 opposite to the radius of curvature R. As illustrated, the device 10 is made preferably of a rod of material, the rod can be solid or hollow, and preferably as illustrated it is a solid rod of material.

Figure 3A:
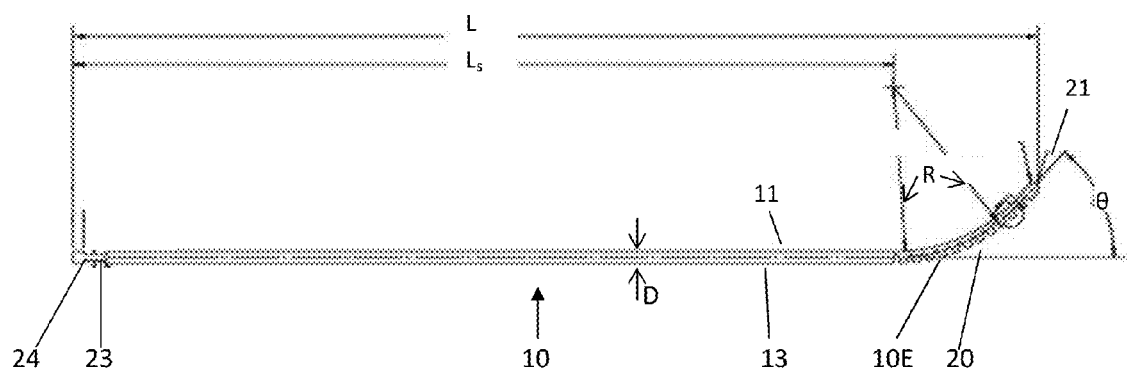
FIG. 3A is a side view of the tunneling device of the present invention.

With reference to FIG. 3A, the length L of the device 10 including the curved end portion 10E extending from one end 21 to the opposite end 24 is sufficient to allow the device 10 to extend outward of the cannula or guide sleeve 100 when in the fully inserted position. The end 24 of the device can be provided with a handle fixed by the flats 23 for an over-molded threaded portion 51 that is housed inside of the handle assembly of the device that prevent rotation in the handle such that the physician can easily push the device in. Furthermore, the handle would indicate the orientation of the curve of the device 10 so that the physician can have an appreciation of the path that the predefined curvature 10P will take when inserted into the guide sleeve 100. This is important because as the device 10 is inserted, the physician wants the curvature to be such that the end portion 10E of the device 10 as it curves crosses the midline of the vertebra 2.

Figure 3B:
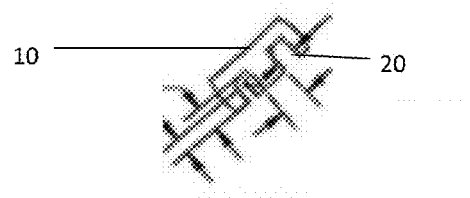
FIG. 3B is an enlarged view of the cut slots on the backside of the present invention.

With reference to FIG. 3B, an enlarged portion of the slots 20 on the back side or opposite side 13 to the radius of curvature R is illustrated. As shown in FIG. 3A, an exemplary device 10 of the present invention has a diameter of 0.0905 inches 2.3 mm and a total straightened length of approximately 8.50 inches, 216 mm and a tangent angle at the maximum point of curvature of 0, 0 being greater than 0 degrees, preferably greater than 30 degrees, more preferably greater than 45 degrees; as shown 50 degrees relative to the straight line of the device 10 itself or the guide sleeve 100 when positioned in the vertebra 2. It is important to note as illustrated, the radius of curvature R is shown as a single radius of curvature R, however, multiple radii of curvature R can be used if so desired and these multiple radii of curvature R can be pre-set into the device 10 similar to a single radius of curvature R. At the very tip or distal end 21 of the tunneling device 10, the rod material that has been rounded to facilitate insertion into the cancellous tissue material 4.

As illustrated in FIG. 3B, the slots 20 created in the back side or opposite side 13 relative to the side 11 of the radius of curvature R are spaced generally uniformly along the curvature R. These slots extend inwardly at or slightly past the midline of the rod, however, leave a sufficient amount of material along the same surface 11 as the radius of curvature R such that the rod when in the straight position inside the guide sleeve 100 has sufficient strength so that it can resist forces that would tend to want to close or work in an opposite direction relative to the pre-set and predefined curvature 10P to the radius of curvature R. This flexibility in the rod enables it to easily slide inside and be easily withdrawn from the cannula. It is important to note that the plurality of slots created along the surface are primarily for flexibility and during insertion it is further noted that the slots when straightened in the guide tube tend to close upon themselves. However, as soon as the rod is free, they return to their natural pre-set and predefined curvature 10P tending to open the slots 20. This is opposite the hinged devices which require the slots to close upon insertion.

Figure 4:
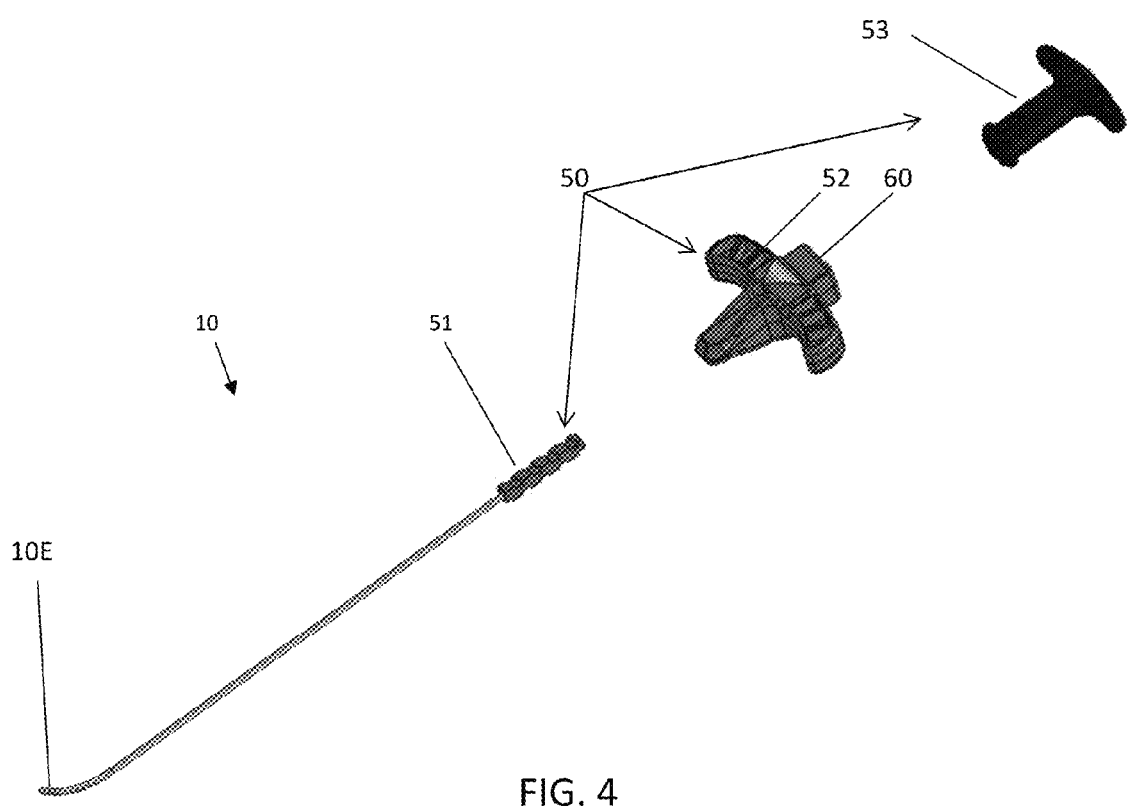
FIG. 4 is an exploded view of the tunneling device of the present invention with an exemplary handle assembly.

As shown in FIG. 4, the tunnel device 10 with the predefined curvature at end portion 10E can have a handle assembly 50. The exemplary handle assembly 50 has a threaded portion 51 secured in a fixed way on the device 10 rod at the distal end opposite the end portion 10E; preferably, it is insert molded over the flats 23 so as to prevent rotation. A handle portion 52 fits onto threaded portion 51 and is fixed so the surgeon can know the orientation of the curved end 10E. The third handle piece 53, possessing internal threads matching the external threads of the threaded portion 51, threaded onto the threaded portion 51 and is fitted into the handle portion 52 round or circular opening 60. The second and third portions fit together on assembly. The third portion 53 can be rotated clockwise to retract the threaded portion 51 further into the handle 52 and retracting shaft 10 and a portion of the curved end 10E back into the guide sleeve 100 to facilitate extraction from the body.

As one can easily appreciate, the slots 20 are provided on that portion of the rod that would normally be under tensile stresses when bent in the direction as illustrated and the smooth portion of the rod adjacent the radius of curvature R would effectively be in compression. However, these materials are generally set at this curvature and therefore the stresses of tensile and compression are not created by the curvature R, but rather there are no compressive or tensile stresses on the device as a result of the pre-set curvature because the device 10 has been made to take this precise shape.

In order to achieve this shape, it was found that a shape memory tunnel device 10 creates an optimal solution for creation of a curved path 10P to cross the midline ML that can be used in this procedure. The path 10P created can be a constant curvature R. Preferably, the predefined curvature R is set to optimize the ability of the surgeon to insert the tunneling device 10 into the cancellous material 4 and to be assured that the path 10P created will follow that curvature such that the balloon tamp 200 when inserted will follow the path 10P created and always be centered and crossing the midline ML of the vertebra 2. The advantages of the present device 10 are that the use of shape set materials means no additional forces such as the bone resistance or mechanisms such as separate tensile members to induce a curvature are needed. The curvature is predefined and already in the device 10 as it is leaving the guide sleeve 100, it returns to its pre-set curvature automatically in the absence of any external resistance or force. In other words, the bone cavity could be filled with air or liquid and the device would simply return to its curved path 10P without any influence or force required. The curved path 10P can be formed as a constant profile and tangent to the working cannula or guide sleeve 100 it is introduced through. The design has the advantage of being constructed from one piece of material and greatly reduces the possibility of device failure or breakage during the procedure. The shape set material can be nitinol, generally a nickel titanium material. However, other materials having shape set capability are known and similarly can be used. These materials can include other metal alloys, metals and polymers that have shape set properties. Furthermore, the shape set material may be induced by using a ferromagnetic shape set material that is responsive to magnetic fields. Or alternatively, can be a temperature set or current set curvature induced device. However, it is important to note that regardless of the type of device used, that it must have the predefined curvature already pre-set when it is positioned in the guide sleeve 100. As further illustrated, it is envisioned that the present device allows the following method to be employed where one would access the vertebral body placing a cannula slightly into a vertebral body just anterior to the posterior wall and keeping the cannula in place creating the passageway with the trocar, removing the trocar and then to insert the tunneling device 10 distal end 10E into the cannula 100, this will straighten the device 10 so that it fits into the cannula 100 relatively easily with minor resistance. And before advancing the device 10 into the vertebra 2, the surgeon will align the curvature portion or path 10P in the desired orientation so that the slots 20 are facing to the outside of the path 10P to be created to ensure that the curvature follows a path that will cross the midline ML of the vertebra 2. The surgeon will then slowly advance the device 10 until the desired midline ML position is achieved. He can observe this using fluoroscope, x ray if so desired. Then without rotating, he will remove the device 10 to leave a midline crossing tunnel for kyphoplasty balloon tamp 200 to follow. The balloon tamp 200 will then be inserted into the cannula or guide sleeve 100 and slowly introduced into the path created by the tunneling device 10 so that the balloon tamp 200 follows the curvature precisely crossing the midline ML of the vertebra 2.

This can all be accomplished with a single entry into the vertebra 2. More importantly due to the construction of the tunneling device 10, the overall diameter (D) of the device 10 can be greatly reduced from what is commonly used. While the device can be of the same size as currently used, it need not be, it can be minimized further if so desired. As a result, a smaller cannula can be used with this procedure.

In the exemplary embodiment, an 11 gauge rod of nitinol material was used. This 11 gauge rod has a diameter of 2.3 mm as a result a cannula of only 2 to 3 mm can be used for this procedure. The limiting factor on using such a small diameter cannula is the ability to provide a balloon tamp 200 sufficiently small to be able to be inflated to the high pressures of 400 psi or more to create the balloon tamp cavity 5. However, assuming that the balloon can mounted on such a small diameter this would reduce the size from the prior art from approximately 11 to 12 mm by a factor of 5 if not 6 times smaller. This greatly reduces the size of the opening 3 which will further accelerate the healing of the patient. It is believed to be the most non-invasive procedure known for kyphoplasty.

It is important to note, that the device 10 of the present invention, while being described is a vast improvement over the current techniques of kyphoplasty, this device 10 can also be used in other procedures and any procedure where a tunneling device is needed to create a curved path 10P. This could include further applications wherein the tunneling device is provided to go into the disc material in between vertebrae and create a tunnel. The tunnels in these cases can be used to clear a path into which medicants or tissue regenerating materials can be injected once a curvilinear path 10P has been created into the disc area. In such a procedure, once the tunneling device 10 is removed a cannula made of a similar curvature would be provided. Preferably the cannula will be a thin walled material of nitinol with a hollow center such that medicants can be injected through the cannula directly into the path inside the disc. These and other procedures are considered possible with the use of a single entry guide sleeve 100 through which a curved component with a pre-set curvature can be provided both for tunneling and for injecting materials into the final location where the surgeon needs to deliver either medicine or bone cement or any other fluid that can be injected into a particular location. As shown, the guide sleeve 100 has been provided in a straight or generally straight configuration. It is believed that the guide sleeve 100 could alternatively have a slight curvature, however it is important to note that this is considered an alternative to straight, however in any event the optimal solution of the present invention is that the tunneling device 10 or cannula 100 depending on the procedure will have a pre-set and predefined curvature that is different and much smaller than any bowed curvature in the guide sleeve 100 and that upon leaving the entry opening 3 into the bone structure the tunneling device 10 or cannula will automatically go back to its pre-set curvature that is different from the path of the guide sleeve 100. This change in path is important in that it creates the ability to increase the curvature of the path created by the tunneling device 10 and/or the path created by the cannula or for later injection of materials.

As used herein, substantially means approximately or very close to the, in the case of a straight line, a straight line.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A tunneling device for introduction into a body via a linearly extending guide, the device comprising: an elongated tunneling device having an end portion with a predefined curvature, the elongated tunneling device when confined in the linearly extending guide is confined lengthwise in the guide; wherein upon movement of the tunneling device advancing past the guide into the body, the end portion of the tunneling device returns to the predefined curvature without requiring any external physical resistance or external load forces to initiate the bending, wherein the tunneling device is an elongated rod, and wherein the rod includes a plurality of cut slots spaced along the rod along the entry portion wherein the slots are on an exterior side of the rod opposite the radius of curvature, wherein the inside surface of the rod adjacent the radius of curvature is smooth and the outside surface aligned with the curvature has the cut slots and upon bending the cut slots open wider.

2. The tunneling device of claim 1 wherein the elongated rod is non-hollow.

3. The tunneling device of claim 1 wherein the predefined curvature of the entry end position has one or more predetermined radius of curvature.

4. The tunneling device of claim 3 wherein the radius of curvature is a constant.

5. The tunneling device of claim 3 wherein a tangent to a maximum curvature at the end or tip is inclined at an angle of 45 degrees or more relative to the straight guide.

6. The tunneling device of claim 3 wherein the final position of a tip of the end portion of the tunneling device is offset from a straight projected path of the linearly extending guide.

7. The tunneling device of claim 1 wherein at least the entry end portion of the tunneling device is made from a shape memory material, the shape memory device having a pre-set memory to bend the entry end portion to the predefined curvature.

8. The tunneling device of claim 7 wherein the shape memory material has a pre-set memory pre-set by heat to the predefined curvature.

9. The tunneling device of claim 8 wherein the shape memory material is a metal or polymer.

10. The tunneling device of claim 9 wherein the shape memory material is a metal alloy.

11. The tunneling device of claim 10 wherein the metal alloy is NiTi (Nickel titanium).

12. The tunneling device of claim 11 wherein the metal alloy is nitinol.

13. The tunneling device of claim 7 wherein the shape memory material is a ferromagnetic shape memory alloy that changes shape under a magnetic field.

* * * * *